(12) United States Patent
Drevik

(10) Patent No.: US 7,147,628 B2
(45) Date of Patent: Dec. 12, 2006

(54) ABSORBENT ARTICLE WITH IMPROVED LIQUID-HANDLING ABILITY

(75) Inventor: Solgun Drevik, Mölnlycke (SE)

(73) Assignee: SCA Hygiene Products AB, Gothenberg (SE)

( * ) Notice: Subject to any disclaimer, the term of this patent is extended or adjusted under 35 U.S.C. 154(b) by 224 days.

(21) Appl. No.: 09/967,918

(22) Filed: Oct. 2, 2001

(65) Prior Publication Data

US 2002/0040211 A1 Apr. 4, 2002

Related U.S. Application Data

(60) Provisional application No. 60/236,744, filed on Oct. 2, 2000.

(51) Int. Cl.
*A61F 13/15* (2006.01)
*A61F 13/20* (2006.01)

(52) U.S. Cl. .................. 604/385.101; 604/385.01; 604/385.24

(58) Field of Classification Search ........ 604/378–379, 604/384, 385.01, 385.101, 385.23, 385.24, 604/385.27, 385.28
See application file for complete search history.

(56) References Cited

U.S. PATENT DOCUMENTS

| | | | | |
|---|---|---|---|---|
| 5,151,091 A | * | 9/1992 | Glaug et al. | 604/385.101 |
| 5,167,654 A | * | 12/1992 | Yang | 604/385.29 |
| 5,181,563 A | * | 1/1993 | Amaral | 604/385.26 |
| 5,569,226 A | * | 10/1996 | Cohen et al. | 604/378 |
| 5,667,609 A | | 9/1997 | Liu | |
| 5,683,374 A | * | 11/1997 | Yamamoto et al. | 604/385.29 |
| 5,766,213 A | * | 6/1998 | Hackman et al. | 604/385.01 |
| 5,895,380 A | * | 4/1999 | Turi et al. | 604/383 |
| 6,171,682 B1 | * | 1/2001 | Raidel et al. | 428/182 |
| 6,436,081 B1 | * | 8/2002 | Wada et al. | 304/385.01 |
| 6,602,234 B1 | * | 8/2003 | Klemp et al. | 604/385.01 |

FOREIGN PATENT DOCUMENTS

| | | |
|---|---|---|
| DE | 4422956 | 1/1996 |
| EP | 649644 | 4/1995 |
| GB | 2284831 | 6/1995 |
| WO | WO 9111161 A1 * | 8/1991 |

* cited by examiner

Primary Examiner—Michele Kidwell
(74) Attorney, Agent, or Firm—Buchanan Ingersoll & Rooney, PC (57) ABSTRACT

An absorbent article (10) such as a sanitary napkin includes an elongate absorbent core (12) delimited by an upper surface (14) and a lower surface (16). A pair of opposed longitudinal edge portions (18, 20) terminates in longitudinal edges (22, 24) and a pair of opposed transverse edges (26, 28). The core has a first end portion (30), a second end portion (32) and a central portion (34) located between the end portions. A liquid permeable topsheet (36) extends over the upper surface (14), and a liquid barrier backsheet (42) covers the lower surface (16) of the absorbent core (12). Leakage barriers (68, 70), each barrier covering a longitudinal edge portion (18, 20) in a respective longitudinal edge portion (18, 20), forms liquid-retaining pockets along each longitudinal edge portion. First spacers are arranged between the absorbent core (12) and each of the leakage barriers (68, 70), and the first spacers are arranged at a distance from each other along the length of the leakage barriers (68, 70) and defines fluid conducting first channels (62), that extends generally perpendicularly to the longitudinal edge portions (18, 20), between the leakage barriers (68, 70) and the absorbent core (12).

36 Claims, 7 Drawing Sheets

ABSORBENT ARTICLE WITH IMPROVED LIQUID-HANDLING ABILITY

CROSS-REFERENCE TO RELATED APPLICATIONS

The present application claims the benefit of U.S. Provisional Application Ser. No. 60/236,744, filed on Oct. 2, 2000, the entire contents of which is hereby incorporated herein by reference.

BACKGROUND OF THE INVENTION

1. Technical Field

The present invention relates to an absorbent article such as a sanitary napkin. The article comprises an elongate absorbent core delimited by an upper surface and a lower surface, a pair of opposed longitudinal edge portions terminating in longitudinal edges, and a pair of opposed transverse edges. The core has a first end portion, a second end portion and a central portion located between said end portions. A liquid permeable topsheet extends over said upper surface, and a liquid barrier backsheet covers said lower surface of said absorbent core. The absorbent article comprises leakage barriers, each barrier covering a longitudinal edge portion in a respective longitudinal edge portion and forms liquid-retaining pockets along each longitudinal edge portion.

2. Discussion of Related Art

A common problem associated with an absorbent article such as a diaper or an incontinence pad, which is intended to absorb body fluid, is that fluid may leak out past the side edges of the article. Such leakage is particularly common when gushes of urine are delivered in a short time period and with a high fluid pressure. During urination, the absorbent core cannot instantly absorb all the fluid, which leads to an excessive amount of fluid that flows over the surface of the absorbent article towards the edges not only in the central portion. To help prevent side leakage, it is customary to arrange different types of leakage barriers along the side edges of the article. For example, diapers and incontinence pads are often provided with elastic members which, while the article is being used, are tightened around the user's body and hold the side edges of the article in sealing contact against the body. Elastic members can also be used to form raised edge barriers. It is also possible to create raised barriers in other ways, for example by providing ridges or the like, which prevent liquid from flowing freely over the side edges of the article. Side leakage barriers may also be in the form of a pair of liquid barrier sheets and a pair of strips of resilient material, that form pockets and increase the stiffness of the sanitary napkin in the region of the mid portion of the absorbent article.

However, it has been found that despite all the efforts, which have hitherto been made to avoid leakage at the side edges, the problem still remains, especially in certain applications. This problem is, for instance, troublesome for bedridden individuals since the risk of leakage increases considerably when the user is lying in a side position. Body fluid which is excreted in this position runs out and gathers, by the effect of gravity, at the longitudinal side edge of the article, where the available absorption material quickly becomes over-saturated with liquid. The remaining liquid that is not absorbed can run freely along the side edge. The risk is of course great that this liquid will be forced out over the side edge of the article and escape if the user moves in such a way that a gap is formed between the article and the user's body.

Conventional hygienic absorbent articles such as sanitary napkins, incontinence pads and the like are provided with an absorbent core which, in theory, is capable of absorbing all the fluid normally discharged by the wearer over an intended exposure time of the article. However, leakage can arise if the absorbent article is not maintained in proper relation with the wearer. One attempt to overcome this problem is to provide a sanitary napkin with so called wings. However, winged sanitary napkins also suffer from certain drawbacks. For example, if a particularly heavy discharge occurs, fluid may spread over the topsheet of the napkin and escape over the wings to thereby stain adjacent clothing. In addition, many wearers regard winged sanitary napkins as being too indiscreet.

Due to their relative narrowness, when sanitary napkins do leak this generally occurs at the side edges. Many attempts have been made to overcome the problem of edge leakage, for example by using strips of resilient material in at least the central portion of the absorbent article which increases the shape stability of the article in the strike zone, i.e., that region of the absorbent article which is first contacted by discharged bodily fluid. In this manner, the risk of bunching of the absorbent article is significantly reduced. In addition, the resilient strips press the longitudinal edges of the absorbent article towards the wearer, thereby causing the article to more readily mould to the body of the wearer. Since the strips need not extend along the entire length of the article, the article may be worn discretely. Advantageously, the remote ends of the strips may serve to impart a bowl-shape to the article to further conform the article to the shape of the wearer.

Standing gathers is a collective name for these different types of elasticated leakage barriers along the side edges of the article, and they suffer from certain drawbacks. For example, if the standing gathers are subject to an excessive amount of external pressure due to, for example, tight trousers, a soft mattress, when the user is in a vertical position or sitting on a bicycle saddle, the standing gathers will be compressed and thereby somewhat closed, whereby the fluid is prohibited from flowing into the pockets formed by the standing gathers.

OBJECTS AND SUMMARY

While absorbent articles having elasticated side barriers may exhibit improved side edge leakage protection when compared to an absorbent article without elasticated side barriers, a need still exists for an absorbent article which further reduces the risk of side edge leakage while still being sufficiently discrete to satisfy the majority of wearers. It is therefore an object of the present invention to provide an absorbent article that meets these requirements.

The present invention relates to an absorbent article such as a sanitary napkin, where the absorbent article comprises an elongate absorbent core delimited by an upper surface and a lower surface, a pair of opposed longitudinal edge portions terminating in longitudinal edges, and a pair of opposed transverse edges. Said core has a first end portion, a second end portion and a central portion located between said end portions. A liquid permeable topsheet extends over said upper surface, and a liquid barrier backsheet covers said lower surface of said absorbent core. Said absorbent article comprises leakage barriers, each barrier covering a longitudinal edge portion in a respective longitudinal edge portion and forms liquid-retaining pockets along each longitudinal edge portion.

The above-stated objects are achieved in accordance with the present invention by an absorbent article in which a part of the absorbent article is profiled and includes spacers arranged at a distance from each other along the length of the upper surface to create fluid conducting first channels.

The profiled parts of the absorbent article may be the longitudinal edge portions, or the entire upper surface. The profiled parts are profiled by groove compression of either the topsheet or the upper part of the absorbent core, or the both together, and the spacers comprise the uncompressed parts of the topsheet and/or the upper part of the absorbent core.

Preferred embodiments will become evident by the subsequent dependent claims.

BRIEF DESCRIPTION OF THE DRAWINGS

The invention will be described in the following by way of example only and with reference to the attached drawings.

DETAILED DESCRIPTION OF PREFERRED EMBODIMENTS

In the figures, the reference numbers that recur in the different figures refer to the same feature, and additional features in different embodiments are designated new reference numbers.

The invention will be presented in a number of different embodiments and will also refer to previously known sanitary napkins, which constitute examples of different known techniques and shall not be seen as limiting for the present invention. The previously known sanitary napkins constitute examples, on which all the embodiments of the invention may be applicable.

Figure 1:
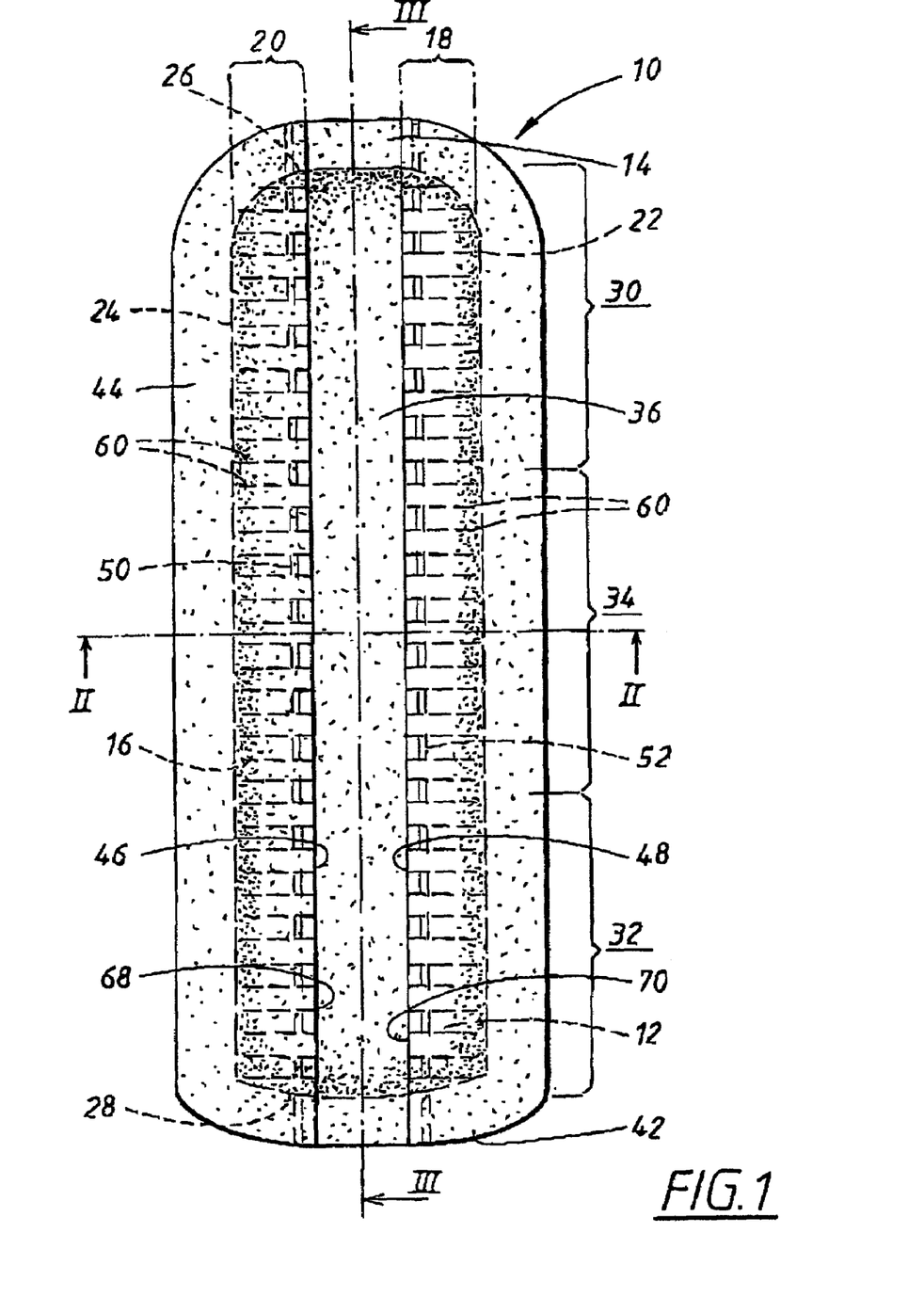
FIG. 1 is a schematic plan view of an absorbent article according to the present invention.
Figure 3:
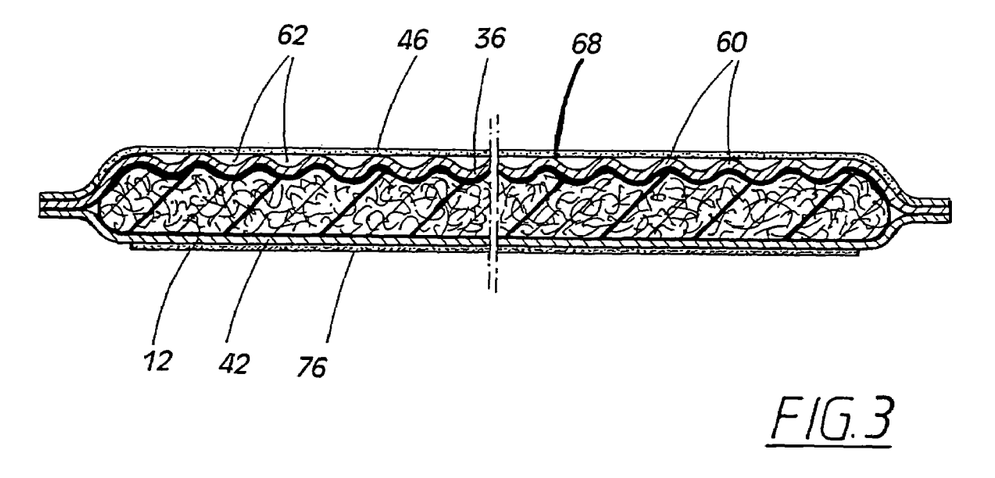
FIG. 3 is a view of a sectional view on a larger scale along line III—III of FIG. 1.

As is apparent from FIG. 1 and 3, reference numeral 10 generally denotes an absorbent article according to the invention. The absorbent article 10 may be a sanitary napkin having an elongate absorbent core 12 delimited by an upper surface 14 and a lower surface 16, and the core 12 may be any conventional absorbent core. The absorbent core further includes opposed longitudinal edge portions 18, 20 terminating in longitudinal edges 22, 24, and a pair of opposed transverse edges 26, 28. The core is made up of a first end portion 30, a second end portion 32 and central portion 34 located between the end portions. In use, the sanitary napkin is intended to be placed relative the wearer so that the strike zone lies within the central portion 34.

As is typical in the art, the absorbent article 10 is further provided with a liquid permeable topsheet 36 extending over the upper surface 14 of the absorbent core 12. The topsheet 36 may be any conventional topsheet. For example, it may be made from a multi-apertured plastic film, or a non-woven material. The absorbent article may also comprise a liquid barrier backsheet 42 extending over the lower surface 16 of the absorbent core 12. The backsheet may be joined to the topsheet 36 to form a peripheral margin 44 around preferably the entire absorbent core 12. On the backsheet 42, there may be fastening means 76 attached for an increased possibility to fasten the absorbent article to the clothing closest to the wearer's body. The fastening means may be an adhesive, mechanical fastening means such as Velcro or another fastening means suitable for the purpose.

The sanitary napkin 10 further comprises a pair of two longitudinal leakage barriers 68, 70, each leakage barrier covering a longitudinal edge portion 18, 20 of the permeable topsheet 36. The leakage barriers 68, 70 each form a liquid-retaining pocket along each longitudinal edge portion 18, 20.

Figure 2:
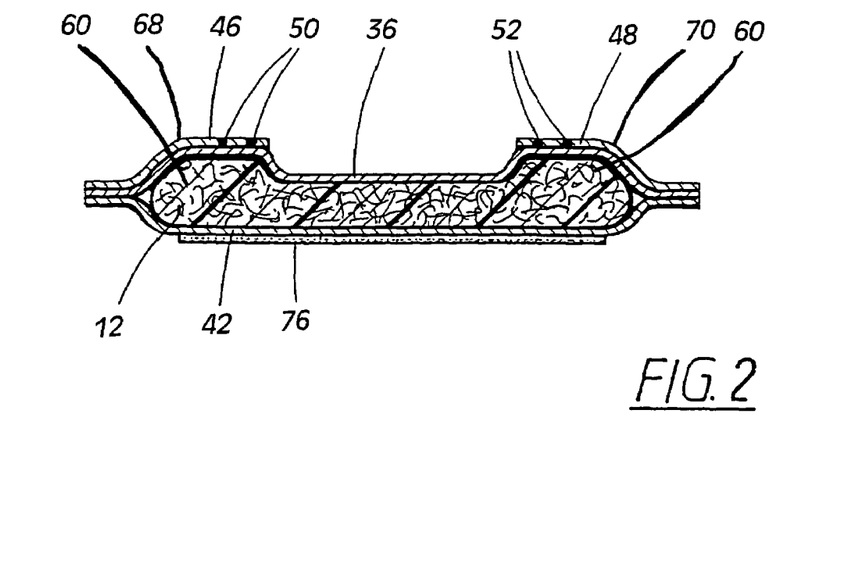
FIG. 2 is a sectional view on a larger scale along line II—II of FIG. 1.

FIGS. 1, 2 and 3 show the invention according to a first embodiment of the invention where a part of the absorbent article 10, such as at least the longitudinal edge portion 18, 20, are made profiled and include first spacing means 60 arranged at a distance from each other along the length of the longitudinal edge portion 18, 20 and will create fluid conducting first channels 62 between the leakage barriers 68, 70 and the top sheet 36 in a direction from the center of the sanitary napkin 10 to the longitudinal sides of the sanitary napkin 10. The first channels 62 are especially advantageous when the leakage barriers 68, 70 are pressed against the top sheet 36 and the upper surface 14 of the absorbent core 12, by an external force, e.g. tight trousers or if the user is sitting down. The first channels 62 then allow migrating body fluids to flow under the leakage barriers 68, 70 even when the leakage barriers 68, 70 are pressed against the top sheet 36, thereby increasing the flow through the absorbent core 12 rather than through the leakage barriers 68, 70 or over the leakage barriers 68, 70. Since the leakage barriers 68, 70 serve to cover the longitudinal edge portions 18, 20, and to seal the sanitary napkin 10 against the user's body, any transport of fluid towards the side of the sanitary napkin is guided via the first channels 62 into the pockets which are formed beneath the leakage barriers 68, 70 and down through the absorbent core 12, even when the leakage barriers 68, 70 are pressed against the top sheet 36, thereby diminishing the risk of side leakage.

Figure 8:
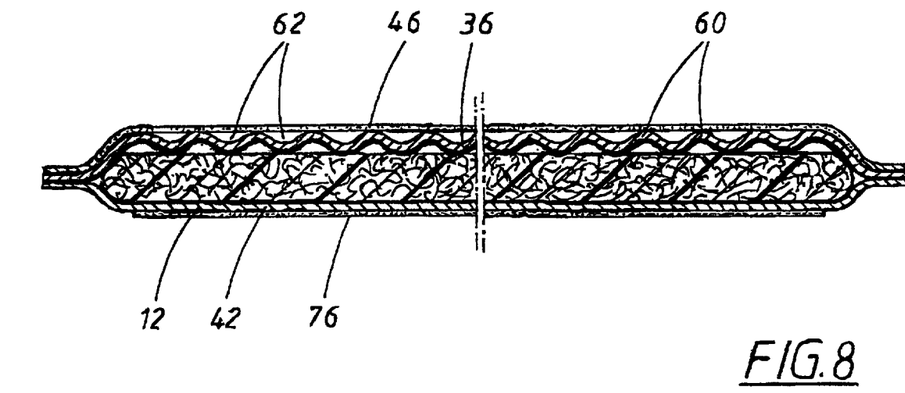
FIG. 8 is a sectional view taken longitudinally on another embodiment of the present invention.

The absorbent article according to a second embodiment of the invention is characterized in that each longitudinal edge portion 18, 20 is profiled by a groove compression of the topsheet 36. The topsheet 36 is formed into a wave pattern of peaks and valleys, with a distance of about 1–15 mm between the peaks, which also defines the width of the first channels, and that the first spacing means 60 consists of the peaks. See, e.g., FIG. 8.

The absorbent article according to a third embodiment of the invention is characterized in that the longitudinal edge portion 18, 20 also may be made profiled by a groove compression of the upper part of the absorbent core 12, and the first spacing means 60 consists of the uncompressed parts. See, e.g., FIG. 6.

A fourth embodiment of the invention is similar to the second embodiment, except that the entire upper surface 14, i.e., including the areas between the longitudinal edge portions 18, 20, is profiled by a groove compression of the topsheet 36.

A fifth embodiment of the invention is similar to the third embodiment, except that the entire upper surface 14, i.e., including the areas between the longitudinal edge portions 18, 20, is made profiled by a groove compression of an upper part of the absorbent core 12, and that the first spacing means 60 consists of the uncompressed parts.

According to a sixth embodiment of the invention, the profiled parts are made profiled by groove compression of both the topsheet 36 and the upper part of the absorbent core 12, and that the first spacing means 60 consists of the uncompressed parts of the topsheet 36 and the upper part of the absorbent core 12. See, e.g., FIG. 3.

Figure 9:
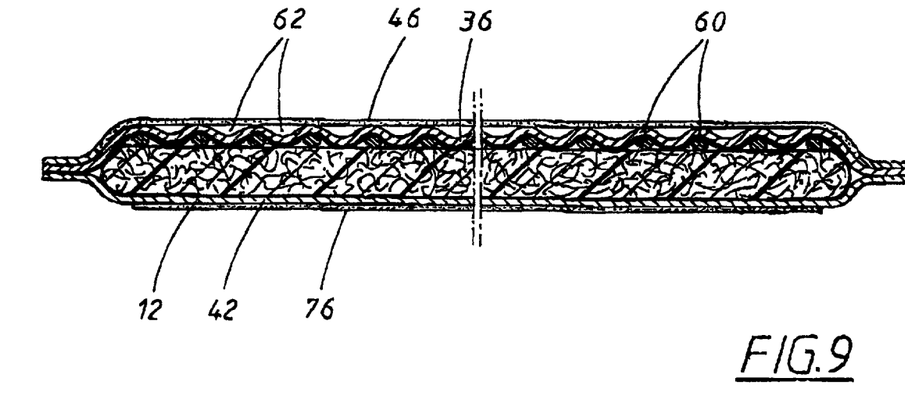
FIG. 9 is a sectional view taken longitudinally on another embodiment of the present invention.
Figure 10:
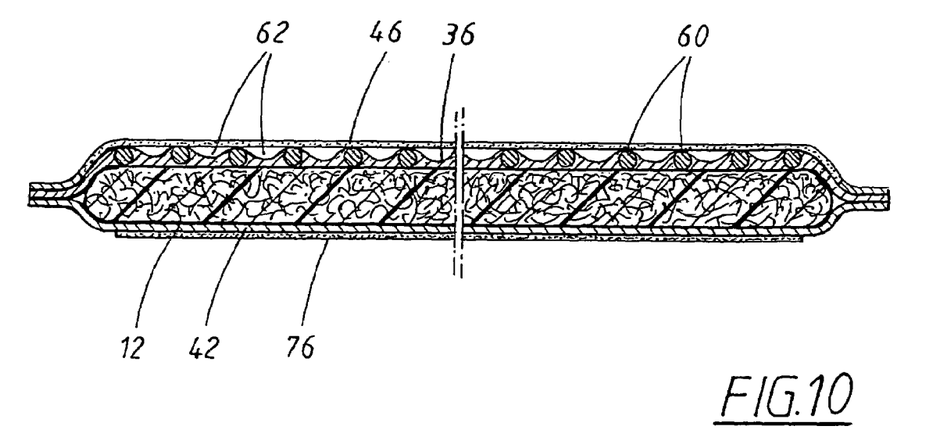
FIGS. 10 and 11 are cross sectional views of other embodiments of the present invention taken along a longitudinal centerline as in FIG. 3.
Figure 11:
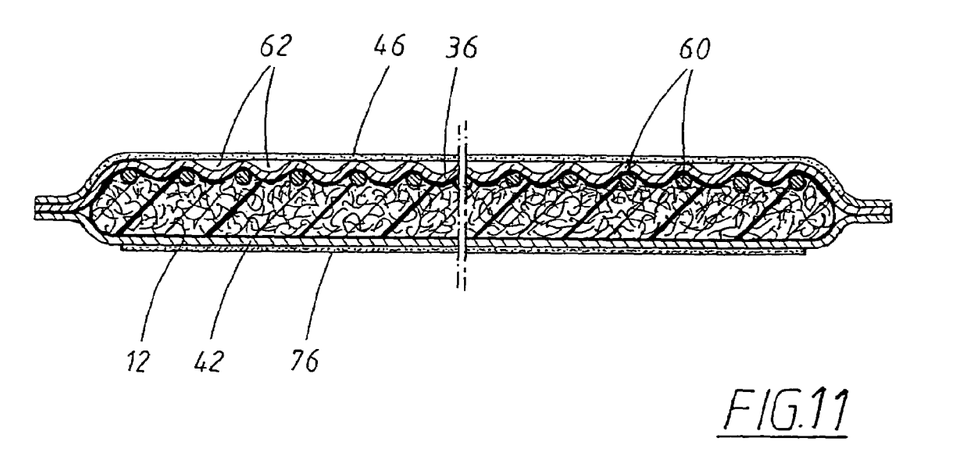

According to a seventh embodiment of the invention, a distance material in the form of cylinders is placed in at least a first area, in a direction from the center of the sanitary napkin 10 to the longitudinal sides of the sanitary napkin 10, and the first spacing means 60 consists of the distance material. See, e.g., FIG. 9.

FIGS. 1, 2 and 3 may be further used as support in the description of yet further embodiments of the invention, where the longitudinal leakage barriers 68, 70 are in the form of barrier strips 46, 48, with each strip covering a longitudinal edge portion 18, 20 of the permeable topsheet 36, that form pockets between the top sheet 36 and the barrier strips 46, 48 along the side edges. The barrier strips 46, 48 may be of either a liquid barrier material or a material that at least resists fluid penetration, e.g., a non-woven hydrophobic fibrous web or another material suitable for the purpose. It is an advantage if the barrier material is breathable, i.e., will permit the passage of air and water vapour. Since the barrier strips 46, 48 may be joined with the peripheral margin 44, the pockets along the edge portions 18, 20 may be seen as enclosed by the barrier strips 46, 48 and the topsheet 36. A pair of pretensioned, longitudinal elastic members 50, 52 are arranged along the barrier strips 46, 48 of the sanitary napkin 10. The elastic members 50, 52 are designed to curve the sanitary napkin 10 to the shape of the user's body and at the same time they constitute means for raising the barrier strips 46, 48 from the upper surface 14 of the sanitary napkin 10. Thus, the elastic members 50, 52 serve to hold the barrier strips 46, 48 of the sanitary napkin 10 in contact against the user's body, in order to ensure that, during use, no gap arises between the sanitary napkin 10 and the user's body, through which gap body fluid could leak from the sanitary napkin 10. Since the material of the barrier strips 46, 48 is primarily hydrophobic, migrating body fluids tend to flow through the absorbent core rather than through the resilient barrier strips 46, 48. Since the barrier strips 46, 48 serve to conceal the longitudinal edge portions 18, 20, any collection of fluid at the edge portions is concealed, thereby imparting an impression of increased safety and cleanliness to the wearer.

Advantageously, the elastic members 50, 52 are made of a three dimensional elastic material such as an elastic polymer, elastic non-woven fibrous plastic, elastic foam, silicone, rubber or another material suitable for the purpose.

Figure 12:
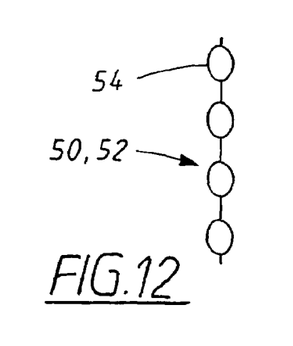
FIGS 12 and 13 illustrate embodiments of the spacing means for embodiments of the present invention.

The elastic members 50, 52 may be in the form of a string of beads 54 (e.g., FIG. 12). The beads serve as second spacing means 160 between the barrier strips 46, 48 and the top sheet 36, and will create fluid conducting second channels (not shown) between the barrier strips 46, 48 and the top sheet 36 in a direction from the center of the sanitary napkin 10 to the longitudinal sides of the sanitary napkin 10. The second channels 62 are especially advantageous when the barrier strips 46, 48 are pressed against the top sheet 36 and the upper surface 14 of the absorbent core 12, by an external force, e.g., tight trousers or if the user is sitting down. The second channels then allow migrating body fluids to flow under the barrier strips 46, 48 even when the barrier strips 46, 48 are pressed against the top sheet 36, thereby increasing the flow through the absorbent core 12 rather than through the barrier strips 46, 48 or over the barrier strips 46, 48. Since the barrier strips 46, 48 serve to cover the longitudinal edge portions 18, 20, and to seal the sanitary napkin 10 against the user's body, any transport of fluid towards the sides of the sanitary napkin is guided via the second channels into the pockets which are formed beneath the barrier strips 46, 48 and down through the absorbent core 12, even when the barrier strips 46, 48 are pressed against the top sheet 36, thereby diminishing the risk of side leakage.

The second spacing means 160 together with the first spacing means 60 will advantageously create channels defined by the combined space of the second channels 162 and the first channels 62, which means that all of the above mentioned advantages with distance material creating channels will be enhanced.

The beads 54 may alternatively have other cross-sectional shapes, such as an oval shape. The beads 54 may also have different diameters and/or different cross sections in the same string of beads.

The string of beads may be created by, for example, point sealing of a three dimensional elastic thread such as an elastic polymer, elastic non-woven fibrous plastic, elastic foam, silicone, rubber or another material suitable for the purpose or two elastic webs with non-elastic spacers between.

Figure 13:
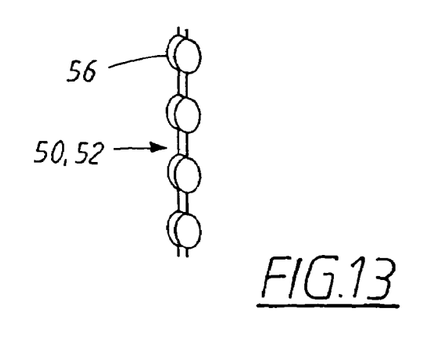
Figure 14:
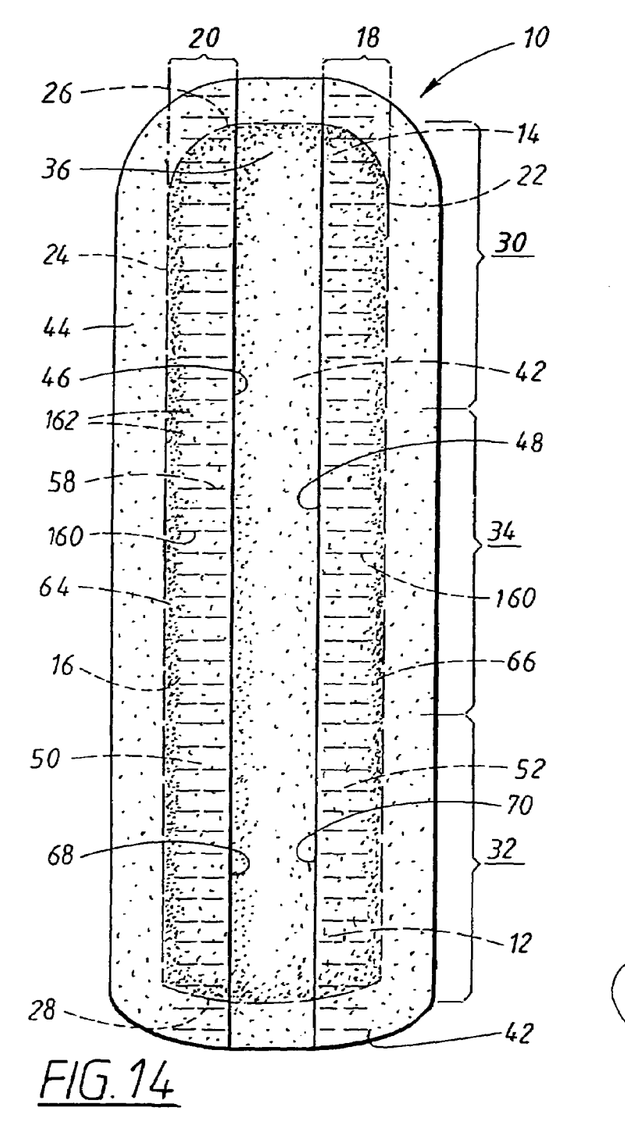
FIG. 14 is a schematic plan view of another embodiment of the present invention.

The elastic members 50, 52 may be broad so that they are in the form of a string of short cylinders 56 (e.g., FIG. 13). The short cylinders serve as second spacing means 160 between the barrier strips 46, 48 and the top sheet 36, and will create second channels 162 between the barrier strips 46, 48 and the top sheet 36 in a direction from the center of the sanitary napkin 10 to the longitudinal sides of the sanitary napkin 10, and serve the same purpose as in the first embodiment. Here, short cylinder means a cylinder having a length less than the cylinder diameter. The cylinder may alternatively have other cross-sectional shapes, such as an oval shape. The cylinders may also have different diameters and/or different cross sections in the same string of cylinders.

The string of short cylinders may be created by, for example, point sealing of a three dimensional elastic thread such as an elastic polymer, elastic non-woven fibrous plastic, elastic foam, silicone, rubber or another material suitable for the purpose or two elastic webs with non-elastic spacers between.

Figure 15:
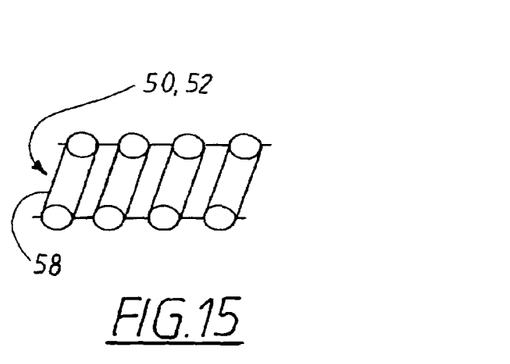
FIG. 15. illustrates another spacing means for embodiments of the present invention.
Figure 16:
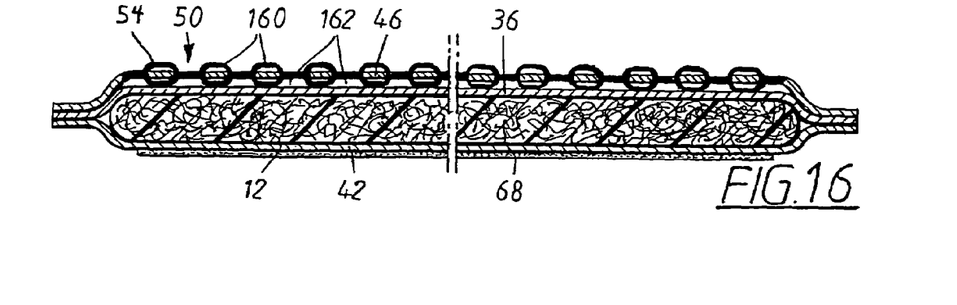
FIG. 16. is a cross sectional view through the embodiment illustrated in FIG. 14 along a longitudinal centerline as in FIG. 3.

The elastic members 50, 52 may be even broader than those forming the short cylinders 56 and are in the form of a string of long cylinders 58 (e.g., FIG. 15). The long cylinders 58 serve as second spacing means 160 between the barrier strips 46, 48 and the top sheet 36, and will create second channels 162 between the barrier strips 46, 48 and the top sheet 36 in a direction from the center of the sanitary napkin 10 to the longitudinal sides of the sanitary napkin 10, and serve the same purpose as in the second embodiment. Here, long cylinder means a cylinder length longer than the cylinder diameter. The cylinder may alternatively have other cross-sectional shapes, such as an oval shape. The cylinders may also have different diameters and/or different cross sections in the same string of cylinders.

The string of long cylinders 58 may be created by, for example, point sealing of a three dimensional elastic thread such as an elastic polymer, elastic non-woven fibrous plastic, elastic foam, silicone, rubber or another material suitable for the purpose or two elastic webs with non-elastic spacers between.

The string of long cylinders may be substituted by a distance material in the form of long cylinders and elastic members, e.g., the elastic members 50, 52 previously mentioned. The cylindrical distance material is placed within the barrier strips 46, 48 or in a manner suitable for the purpose of using the distance material to create second channels between the barrier strips 46, 48 and the top sheet 36 in a direction from the center of the sanitary napkin 10 to the longitudinal sides of the sanitary napkin 10. The elastic members 50, 52 may be a pair of pretensioned, longitudinal elastic members 50, 52 that are arranged along the barrier strips 46, 48 of the sanitary napkin 10. The elastic members 50, 52 are designed to curve the sanitary napkin 10 to the shape of the user's body and at the same time they constitute means for keeping open the side pockets created beneath the barrier strips 46, 48 and the sanitary napkin 10.

The distance material in the form of long cylinders 58 according to the above-mentioned embodiment of the invention may alternatively have other cross-sectional shapes, such as an oval shape. The distance material may also have different diameters and/or different cross sections in the barrier strips 46, 48.

The long cylinders may be a three dimensional elastic thread such as an elastic polymer, elastic non-woven fibrous plastic, elastic foam, silicone, rubber or another material suitable for the purpose or two elastic webs with non-elastic spacers between.

The short and the long cylinders may be up to 50 mm long.

The distance between the second spacing means, i.e., the width of the second channel, is 1–20 mm.

Figure 4:
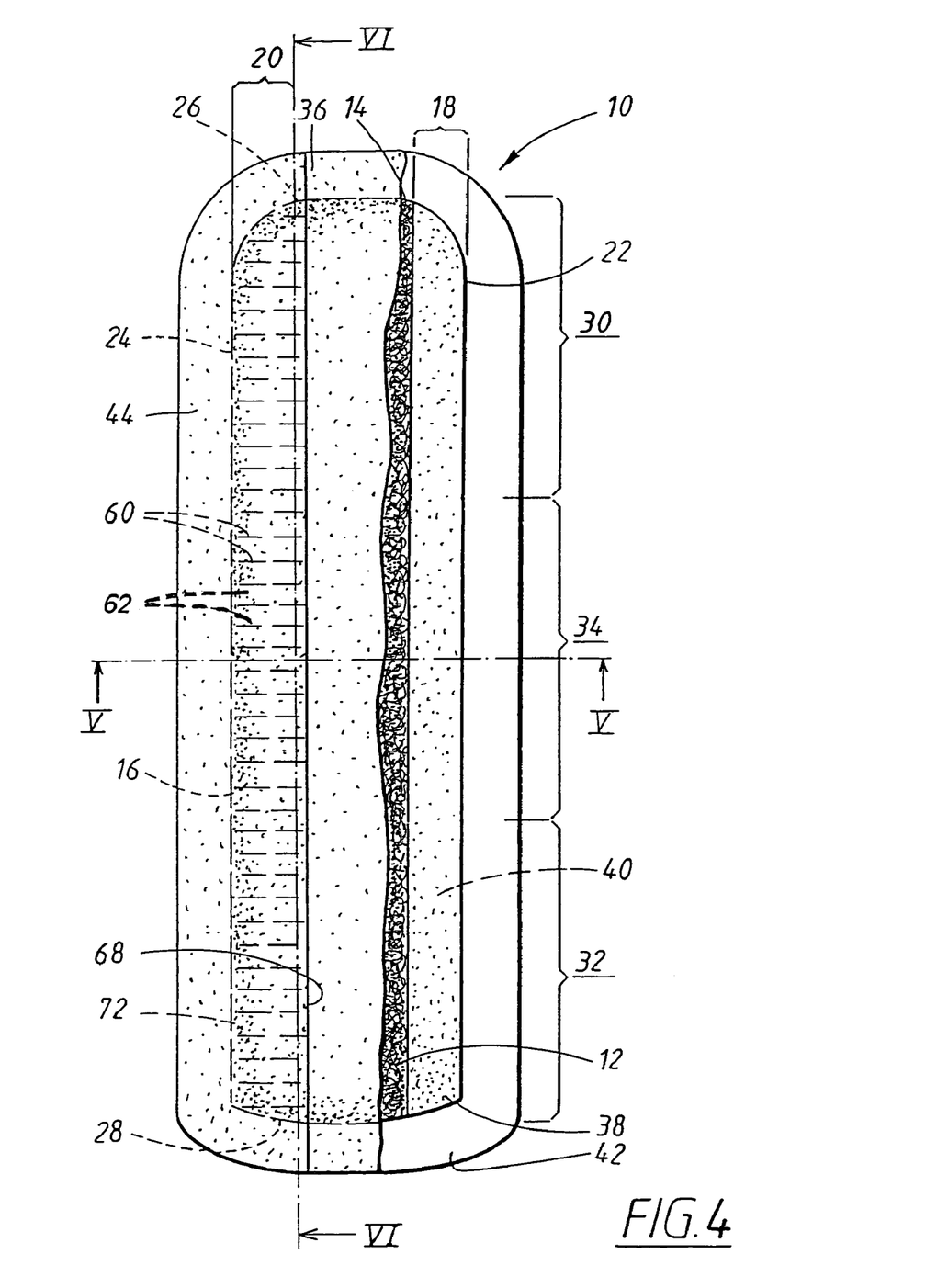
FIG. 4 is a schematic plan view of an absorbent article according to a second embodiment of the present invention with a partially cut away topsheet.
Figure 5:
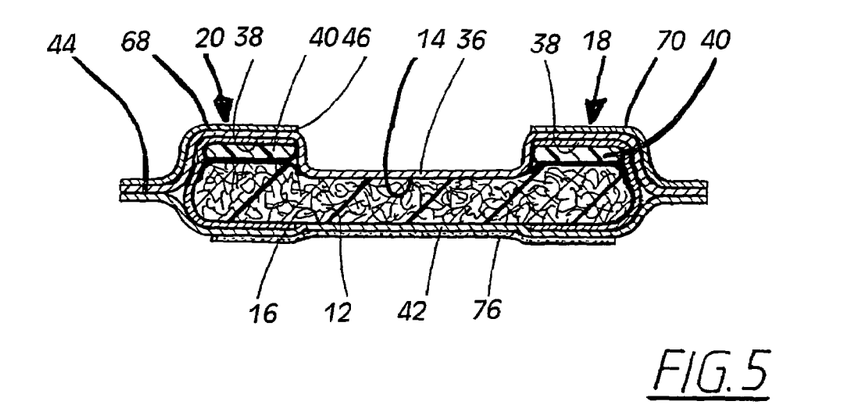
FIG. 5 is a sectional view on a larger scale along line V—V of FIG. 4.
Figure 6:
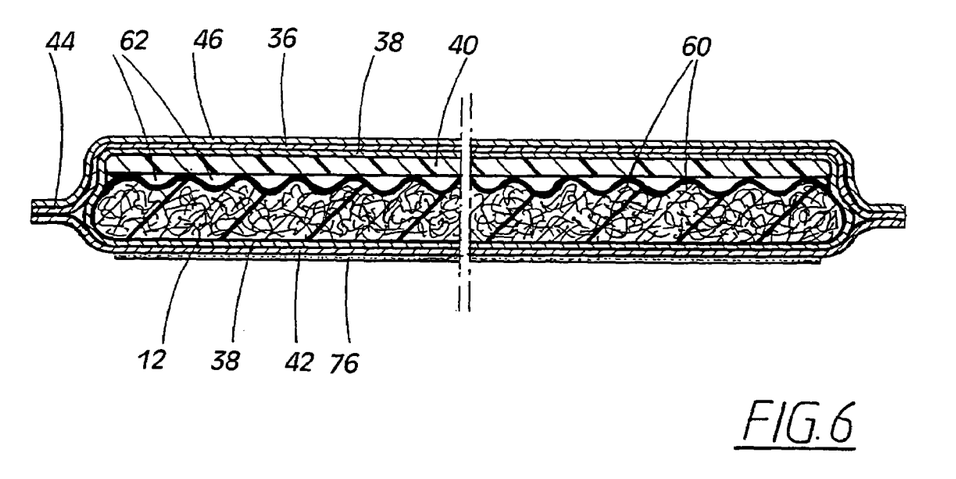
FIG. 6 is a view of a sectional view on a larger scale along line VI—VI of FIG. 4.

FIGS. 4, 5 and 6 show the invention combined with a previously known sanitary napkin and as is typical in the art. The absorbent article 10 comprises leakage barriers 68, 70 in the form of a pair of liquid barrier sheets 38 and a pair of strips of resilient material 40, with each liquid barrier sheet 38 covering a longitudinal edge portion 18, 20. The strips of resilient material 40 may be placed either over or under the top sheet 36, but in the figures the strips of resilient material 40 are placed under the top sheet 36, which also will be described in the following embodiments. The liquid barrier sheets 38 may be placed either over or under the top sheet, but in the figures the strips of liquid barrier sheets 38 are placed under the top sheet 36, which also will be described in the following embodiments. The liquid barrier sheets 38 are preferably coated with adhesive on their concave surface, i.e., the surface facing towards the absorbent body. Although a pair of separate barrier sheets 38 has been shown in the drawings, it is to be realized, however, that the two sheets 38 may be replaced by a single sheet extending over the entire lower surface 16 of the absorbent core, being folded over the longitudinal edges 22, 24 and covering the longitudinal edge portions 18, 20.

In this previously known sanitary napkin it is also known, and as best illustrated in FIG. 4, 5 and 6, that the strip of resilient material 40 is placed between each liquid impermeable sheet 38 and the absorbent core 12 along each longitudinal edge portion 18, 20 of the absorbent core in at least the mid portion 34 of the absorbent core. The strips of resilient material 40 serve to significantly increase the stiffness of the sanitary napkin in the region of the mid portion. In other words, the resistance to flexure in the longitudinal direction is increased by at least 10% in the longitudinal edge portions in the mid portion when compared to a sanitary napkin without strips of resilient material.

Advantageously, the strips of resilient material 40 are primarily hydrophobic and may be a three dimensional non-woven fibrous plastic wadding or a foamed plastic. Since the material of the strips is primarily hydrophobic, migrating body fluids tend to flow through the absorbent core rather than though the strips of resilient material. Since, in the embodiment shown in FIG. 5, the strips of resilient material 40 serve to conceal the longitudinal edge portions 18, 20 in the mid portion 34, any collection of fluid at the edge portions is concealed, thereby imparting an impression of increased safety to the wearer.

Figure 7:
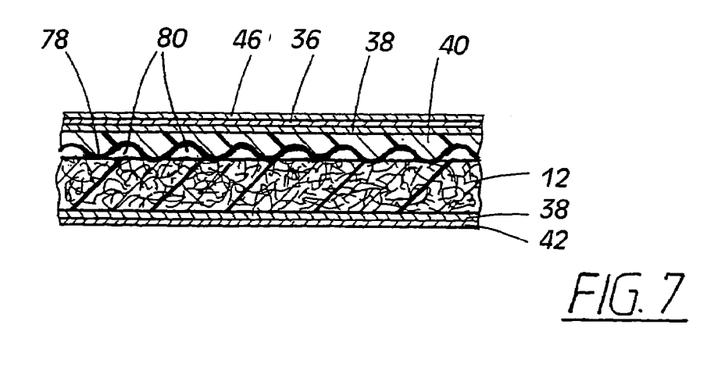
FIG. 7 is a sectional view taken longitudinally on another embodiment of the present invention.

According to another embodiment of the invention, the strips of resilient material 40 may also be profiled by groove compressions on the surface that faces the upper side of the absorbent core 12. Thus, the strips of resilient material 40 include third spacing means 78 in the form of uncompressed resilient material arranged at a distance from each other along the length of the resilient material 40 to create third fluid conducting third channels 80 between the strips of resilient material 40 and the absorbent core 12, and the third spacing means 78 consists of the uncompressed parts of the resilient material 40. See, e.g., FIG. 7.

In a further embodiment of the previously known sanitary napkin, strips of resilient material 40 are placed between the liquid impermeable sheets 38 and the lower surface 16 of the absorbent core 12. Preferably, however, the strips of resilient material are placed between the liquid impermeable sheets 38 and the upper surface 14 of the absorbent core. In this manner, the strips of resilient material 40 serve to "lift" the liquid impermeable sheets 38 from the upper surface 14 of the absorbent core to thereby create an opening to a liquid-retaining pocket formed by the liquid impermeable sheet 38 along each longitudinal edge portion 18, 20. Accordingly, any discharged bodily fluids which migrate across the upper surface of the absorbent core will flow through the opening and into the liquid-retaining pocket. Due to the fact that the concave surfaces of the strips of resilient material 40 are coated with adhesive and thereby adhere to the absorbent core 12 and the liquid-impermeable sheet 38, the risk of fluids leaking from the liquid-retaining pockets is minimal.

Particularly in the case when the absorbent article comprises a pair of liquid impermeable sheets 38 covering the longitudinal edge portions 18, 20 of the absorbent core 12, the absorbent article may also include a liquid impermeable backsheet 42 extending over the lower surface 16 of the absorbent core. Preferably, the backsheet 42 is made of the same material as the liquid impermeable sheet 38 and is joined to the topsheet 36 to form a peripheral margin 44 around preferably the entire absorbent core 12. In this manner, the liquid-retaining pockets along the edge portions 18, 20 are enclosed by the topsheet 36 and the backsheet 42.

For ease of manufacturing and to ensure that the risk of edge leakage anywhere along the length of the absorbent article is minimal, the liquid retaining pockets preferably extend along the entire length of the absorbent core 12. Since, however, the form stability of the absorbent article is most critical only in the mid portion 34 of the absorbent core, the strips of resilient material 40 need only occupy said mid portion. However, if desired, the strips may extend into the first and second end portions 30, 32.

The pockets may extend along the entire length of said absorbent core 12, or extend along the central portion 34 of said absorbent core 12.

The absorbent article according to any one of the preceding embodiments is characterized in that the thickness of the first, second and third spacing means is preferably at least 1 mm, and that the sum of the thickness of the first and second spacing means or the first and third spacing means or the second and the third spacing means defines the respective combination's maximum height of the sum of the first channel and/or second channel and/or third channel. The thickness of the spacing means also means the diameter when the spacing means are cylindrical or spherical.

The distance between the third spacing means 78, i.e., the width of the third channels, is 1–15 mm.

Advantageously, the mid portion 34 of the absorbent core 12 comprises between 20% and 60%, preferably between 30 and 45%, and most preferably about one third, of the length of the absorbent core.

Obviously, the hydrophobic strips of resilient material 40 or the barrier strips 46, 48, i.e., the leakage barriers 68, 70 may not extend over the entire width of the absorbent core since this would prevent passage of body fluids into the absorbent core 12. Accordingly, the leakage barriers 68, 70 have an extension transversely across the absorbent core, with the extension being between 5% and 25% of the total width of the sanitary napkin at the wetting area. The liquid impermeable sheets 38 advantageously display the same or similar transverse extension as the strips of resilient material. The thickness of the strips of resilient material 40, i.e., the extension of the strips in a direction substantially perpendicular to the upper surface of the absorbent core, should be sufficient to allow the strips to mould to the wearer's body. Typically, the thickness of the strips in an uncompressed condition can thus lie between about 1 and 5 mm.

The invention is not restricted to the embodiments described above and shown in the drawings, but may be modified within the scope of the appended claims. For example, strips of resilient material may be placed on both surfaces of the absorbent core in the longitudinal edge portions.

The absorbent article may be a sanitary napkin, a diaper, an incontinent protection article, a panty liner or any absorbent article suitable for the purpose. The absorbent article is not restricted to any shape or configuration, but may be of any shape suitable for the purpose, e.g., triangular, hourglass shaped or rectangular. Also, the elastic members and the distance material may be of a stiff material, and the side barriers with the distance material will still create the channels for transporting the fluids. The sanitary napkin may also be equipped with wings.

In making a sanitary napkin in a shape other than the one shown in the figures, preferably the topsheet 36 will not extend outside the absorbent core, and the backsheet 42 or the liquid impermeable sheet 38 will not together with the topsheet 36 form a peripheral margin 44, but the backsheet 42 or the liquid impermeable sheet 38 will be folded over the side edges over the topsheet. The barrier strips 46, 48, in the embodiments referring to FIGS. 4, 5, 6 or 7 may be excluded, and shall only be seen as a possibility to reinforce and/or modify the sanitary napkin according to certain needs.

The elastic members not only serve as means for creating channels, but may also bend the sanitary napkin into a cup-shape with the whetting area as one of the low points.

There may also be a combination of the above-described embodiments of the invention. For instance, the resilient material 40 may be profiled at the same time as the absorbent core, together creating fluid conducting channels.

Although only preferred embodiments are specifically illustrated and described herein, it will be appreciated that many modifications and variations of the present invention are possible in light of the above teachings and within the purview of the appended claims without departing from the spirit and intended scope of the invention.

What is claimed is:

1. An absorbent article, comprising:
    an elongate absorbent core having an upper surface and a lower surface, a pair of opposed longitudinal edge portions terminating in longitudinal edges, and a pair of opposed transverse edges, the core having a first end portion, a second end portion and a central portion located between the end portions;
    a liquid permeable topsheet extending over the upper surface;
    a liquid barrier backsheet covering the lower surface of the absorbent core,
    leakage barriers, a respective one of the leakage barriers covering each of the longitudinal edge portions and forming a liquid-retaining pocket along each longitudinal edge portion, wherein the leakage barriers each have an extension transversely across the absorbent core, the extension being between 5% and 25% of the total width of the sanitary napkin at the wetting area; and
    first spacers arranged between the absorbent core and each of the leakage barriers, the first spacers being arranged at a distance from each other along a length of the leakage barriers so as to form fluid conducting first channels between the leakage barriers and the absorbent core,
    wherein the first spacers have a length and a width, wherein the width is the dimension between two adjacent first channels and the length is the dimension perpendicular to the width,
    wherein the first spacers extend, in the length-wise direction of the first spacers, generally perpendicularly to the longitudinal edge portions,
    wherein the first channels have a length and a width, wherein the width is the dimension between two adjacent first spacers and the length is the dimension perpendicular to the width,
    wherein the first channels extend, in the length-wise direction of the first channels, generally perpendicularly to the longitudinal edge portions.

2. The absorbent article according to claim 1, wherein each longitudinal edge portion of the absorbent core is profiled.

3. The absorbent article according to claim 1, wherein the upper surface is profiled.

4. The absorbent article according to claim 1, wherein the topsheet is profiled by groove compressions, and the first spacers comprise uncompressed parts of the topsheet.

5. The absorbent article according to claim 3, wherein the first spacers comprise uncompressed parts of the absorbent core.

6. The absorbent article according to claim 3, wherein both the topsheet and the upper surface of the absorbent core are profiled by groove compression, and the first spacers comprise uncompressed parts of the topsheet and the upper surface of the absorbent core.

7. The absorbent article according to claim 1, wherein the first spacers comprise a distance material in the form of cylinders, that are placed in the topsheet in a direction from a center of the absorbent article to the longitudinal edges of the absorbent article.

8. The absorbent article according to claim 1, wherein the first spacers comprise a distance material in the form of cylinders, that are placed in the upper surface in a direction from a center of the absorbent article to the longitudinal edges of the absorbent article.

9. The absorbent article according to claim 1, wherein the leakage barriers comprise barrier strips, each barrier strip covering a respective longitudinal edge portion and forming liquid-retaining pockets along each longitudinal edge portion, a pair of longitudinal elastic members are arranged along the barrier strips that are placed along each longitudinal edge portion of the absorbent core in at least the central portion of the absorbent core.

10. The absorbent article according to claim 9, wherein the elastic members are in the shape of a string of beads, and the beads form second spacers.

11. The absorbent article according to claim 9, wherein the elastic members are in the shape of a string of cylinders having a length less than a cylinder diameter, and the cylinders form second spacers.

12. The absorbent article according to claim 9, wherein the elastic members are in the shape of a string of cylinders having a length longer than a cylinder diameter, and that the cylinders form second spacers.

13. The absorbent article according to claim 12, wherein a thickness of the second spacers is at least 1 mm.

14. The absorbent article according to claim 9, wherein a distance material in the form of cylinders are placed within the barrier strips in a direction from a center of the absorbent article to the longitudinal edges of the absorbent article.

15. The absorbent article according to claim 9, wherein the barrier strips are primarily hydrophobic.

16. The absorbent article according to claim 9, wherein the longitudinal elastic members are a three dimensional non-woven fibrous plastic wadding or a foamed plastic.

17. The absorbent article according to claim 1, further comprising a liquid impermeable sheet covering the longitudinal edge portions of the absorbent core and each of the leakage barriers comprises a strip of resilient material that is placed between the liquid impermeable sheet and the absorbent core along each longitudinal edge portion of the absorbent core in at least the mid portion of the absorbent core to thereby increase the flexure resistance of the article.

18. The absorbent article according to claim 17, wherein a side of the strip of resilient material that faces the upper side of the absorbent core is profiled by groove compression.

19. The absorbent article according to claim 18, wherein uncompressed profiled parts of the strip of resilient material form third spacers.

20. The absorbent article according to claim 19, wherein a thickness of the third spacers is at least 1 mm.

21. The absorbent article according to claim 17, wherein the strip of resilient material is a three dimensional non-woven fibrous plastic wadding or a foamed plastic.

22. The absorbent article according to claim 17, wherein the strip of resilient material is placed between the liquid impermeable sheet and the lower surface of the absorbent core.

23. The absorbent article according to claim 17, further comprising a pair of liquid impermeable sheets, each sheet covering a respective longitudinal edge portion and forming liquid-retaining pockets along each longitudinal edge portion.

24. The absorbent article according to claim 19, wherein the liquid barrier backsheet and the topsheet are joined to form a peripheral margin around the absorbent core to thereby enclose the liquid-retaining pockets along the edge portions.

25. The absorbent article according to claim 23, wherein the pockets extend along an entire length of the absorbent core.

26. The absorbent article according to claim 23, wherein the pockets extend along only the central portion of the absorbent core.

27. The absorbent article according to claim 1, wherein the central portion of the absorbent core comprises between 20% and 60% of the absorbent core.

28. The absorbent article according to claim 1, wherein a thickness of the first spacers is at least 1 mm.

29. The absorbent article according to claim 1, wherein the absorbent article is a sanitary napkin.

30. The absorbent article according to claim 1, wherein the central portion of the absorbent core comprises between 30% and 45% of the absorbent core.

31. The absorbent article according to claim 1, wherein the central portion of the absorbent core comprises about one-third of the absorbent core.

32. An absorbent article, comprising:
an elongate absorbent core having an upper surface and a lower surface, a pair of opposed longitudinal edge portions terminating in longitudinal edges, and a pair of opposed transverse edges, the core having a first end portion, a second end portion and a central portion located between the end portions;
a liquid permeable topsheet extending over the upper surface;
a liquid barrier backsheet covering the lower surface of the absorbent core,
leakage barriers, a respective one of the leakage barriers covering each of the longitudinal edge portions and forming a liquid-retaining pocket along each longitudinal edge portion, wherein the leakage barriers each have an extension transversely across the absorbent core, the extension being between 5% and 25% of the total width of the sanitary napkin at the wetting area; and
channels arranged between the absorbent core and each of the leakage barriers, the channels being arranged at a distance from each other along a length of the leakage barriers so as to conduct fluid between the leakage barriers and the absorbent core,
wherein the channels have a length and a width, wherein the width is the dimension between two adjacent first spacers and the length is the dimension perpendicular to the width,
wherein the channels extend, in the length-wise direction of the channels, generally perpendicularly to the longitudinal edge portions.

33. The absorbent article according to claim 32, further comprising a liquid impermeable sheet covering the longitudinal edge portions of the absorbent core and each of the leakage barriers comprises a strip of resilient material that is placed between the liquid impermeable sheet and the absorbent core along each longitudinal edge portion of the absorbent core in at least the mid portion of the absorbent core to thereby increase the flexure resistance of the article.

34. The absorbent article according to claim 33, wherein the strip of resilient material is a three dimensional nonwoven fibrous plastic wadding or a foamed plastic.

35. The absorbent article according to claim 33, wherein the strip of resilient material is placed between the liquid impermeable sheet and the lower surface of the absorbent core.

36. The absorbent article according to claim 33, wherein the liquid impermeable sheets form liquid-retaining pockets along each longitudinal edge portion.

* * * * *